(12) United States Patent
Sturm et al.

(10) Patent No.: US 9,023,290 B2
(45) Date of Patent: May 5, 2015

(54) CONTAINER FOR A CONTACT LENS STORAGE SOLUTION AND CLEANING AND/OR STERILIZING DEVICE FOR CONTACT LENSES IN A CONTACT LENS STORAGE SOLUTION

(76) Inventors: Albert Sturm, Cologne (DE); Yves Nold, Paris (FR)

( * ) Notice: Subject to any disclaimer, the term of this patent is extended or adjusted under 35 U.S.C. 154(b) by 85 days.

(21) Appl. No.: 13/879,158

(22) PCT Filed: Oct. 17, 2011

(86) PCT No.: PCT/EP2011/068074
§ 371 (c)(1),
(2), (4) Date: Jul. 1, 2013

(87) PCT Pub. No.: WO2012/049323
PCT Pub. Date: Apr. 19, 2012

(65) Prior Publication Data
US 2013/0280142 A1 Oct. 24, 2013

(30) Foreign Application Priority Data

Oct. 15, 2010 (EP) ..................................... 10187698
Jan. 27, 2011 (EP) ..................................... 11152402

(51) Int. Cl.
*B01D 11/04* (2006.01)
*B01D 11/02* (2006.01)
(Continued)

(52) U.S. Cl.
CPC ............... *A45C 11/005* (2013.01); *A61L 12/08* (2013.01); *A61L 12/12* (2013.01); *G02C 13/008* (2013.01)

(58) Field of Classification Search
CPC .................................. A61L 2/00; A61L 12/00

USPC ............... 422/1, 40, 256, 261, 292, 300, 305; 206/5.1, 439, 217, 203–204, 366–367, 206/251; 220/23.83, 23.91, 500, 694; 222/565, 556
See application file for complete search history.

(56) References Cited

U.S. PATENT DOCUMENTS 3,473,886 A 10/1969 Leeds
4,637,919 A 1/1987 Ryder et al.
(Continued)

FOREIGN PATENT DOCUMENTS

CA 2120628 A1 4/1993
DE 20 2009 003699 U1 8/2010

OTHER PUBLICATIONS

International Search Report corresponding to PCT/EP2011/068074 dated Dec. 12, 2011.

*Primary Examiner* — Monzer R Chorbaji
(74) *Attorney, Agent, or Firm* — Renner, Otto, Boisselle & Sklar, LLP (57) ABSTRACT

The invention relates to a container for a contact lens storage solution, in particular having contact lenses in said contact lens storage solution. The container has a vessel (14), which has a filling opening (20), and a first closing element (24), which can be attached to the vessel (14) and which closes the filling opening (20). The first closing element (24) has a gas supply channel (42) for a cleaning and/or sterilizing gas, which extends from at least one inlet (40) on an outer face of the first closing element (24) to at least one outlet (48) on an inner face of the first closing element (24) facing the interior of the vessel (14). On the outer face of the first closing element, said first closing element (24) has at least one venting opening (50) for the escape of gas from the vessel (14). The invention further relates to a container for a contact lens storage solution, which has a second closing element (26) which is arranged on the first closing element (24) and which closes the at least one inlet (40) of the gas supply channel (42) and the at least one venting opening (50) of the first closing element (24).

18 Claims, 7 Drawing Sheets

(51) Int. Cl.
 *A45C 11/04* (2006.01)
 *A47G 19/00* (2006.01)
 *A45C 11/00* (2006.01)
 *A61L 12/08* (2006.01)
 *A61L 12/12* (2006.01)
 *G02C 13/00* (2006.01)

(56) References Cited

U.S. PATENT DOCUMENTS

2007/0215652 A1  9/2007  Rockow
2009/0229999 A1* 9/2009  Haggin .......................... 206/5.1

* cited by examiner

CONTAINER FOR A CONTACT LENS STORAGE SOLUTION AND CLEANING AND/OR STERILIZING DEVICE FOR CONTACT LENSES IN A CONTACT LENS STORAGE SOLUTION

The invention relates to a container for a contact lens storage solution, in particular having contact lenses in said contact lens storage solution. The invention further relates to a cleaning and/or sterilizing device for contact lenses arranged in a contact lens storage solution.

The cleaning of contact lenses, particularly soft contact lenses, can be performed by various systems. Of widespread use for this purpose are aqueous systems wherein a dissolved oxidative reagent acts on the contact lens and has to be removed afterwards. Normally, the oxidative reagent used herein is active oxygen, e.g. in the form of hydrogen peroxide or ozone. In the first case, the excess hydrogen peroxide has to be destroyed by the addition of other reagents, in order to avoid that contact lenses which were accidentally contaminated by hydrogen peroxide are supplied to the user. As hydrogen peroxide-destroying agents, use is made of reducing agents such as sodium thiosulfate, which in turn must be rinsed again. Better suited under the practical aspect is the use of ozone, since this will obviate the need for the bothersome destruction of the hydrogen peroxide.

EEP 968 003 B1 discloses an efficient cleaning of contact lenses by the simultaneous use of proteases and hydrogen peroxide. In this case, proteases will destroy tenacious protein deposits in the contact lenses, and the hydrogen peroxide will disinfect the contact lens which has been cleansed thereafter. A disadvantage also herein resides in the use of hydrogen peroxide, which has to be neutralized.

Another disadvantage of the use of hydrogen peroxide is its instability, as it slowly decomposes into water and oxygen during storage. This is especially important in countries with high average temperatures.

It would be desirable that the above described cleaning of contact lenses could be performed in a container internally of which the contact lenses to be cleaned are arranged in a storage solution. Such a container could be taken along by the person needing the contact lenses and then, for the purpose of cleaning the contact lenses, be connected to a hydrogen peroxide or ozone generator. Generators of this type are generally known and commercially available.

Known from DE 20 2009 003 699 U1 is a container for a contact lens storage solution, in particular with contact lenses in said contact lens storage solution, wherein, via automatically openable and closeable valves, a gassing process using a cleaning and/or sterilizing gas can be carried out when the container has been placed in the receiving chamber of a generator for generating a cleaning and/or sterilizing gas.

It is an object of the invention to provide a container for a contact lens storage solution, which is conveniently suited for supply of a cleaning/sterilizing gas.

To achieve this object, there is proposed, according to the invention, a container for a contact lens storage solution, in particular having contact lenses in said contact lens storage solution, said container comprising
- a vessel having a filling opening,
- a first closing element attachable to the vessel for closing the filling opening,
- the first closing element comprising a gas supply channel for a cleaning and/or sterilizing gas, which extends from at least one inlet on an outer face of the first closing element to at least one outlet on an inner face of the first closing element facing the interior of the vessel, and
- said first closing element comprising, on its outer face, at least one venting opening for the escape of gas from the vessel, and
- a second closing element arranged on the first closing element, for closing the at least one inlet of the gas supply channel and the at least one venting opening of the first closing element.

According to the invention, the container comprises a "dual closure system" which includes a first and a second closure element. The first closure element serves for closing the filling opening of the vessel and comprises a gas supply channel extending between an inlet and an outlet through the closure element. Said inlet as well as said outlet are selectively closeable with the aid of the second closure element.

Handling of the container of the invention is extremely simple. For transport of the container inclusive of the storage solution and the contact lenses arranged in said solution, the filling opening is in a tightly sealed state with the aid of the first closure element while the second closure element closes the inlet and the outlet of the gas supply channel of the first closure element. If, now, a cleaning and respectively sterilizing gas is to be introduced into the vessel, it is merely required to expose or open the inlet of the gas supply channel of the first closure element and to open the outlet by moving the second closure element from the closing position into the opening position. For filling the vessel with storage solution and respectively for removing the contact lenses or for inserting the contact lenses, the first closure element will be transferred from its closing position in which it closes the filling opening, into its opening or release position in which the venting opening is exposed.

For gassing the vessel, the vessel will be inserted into a cleaning and/or sterilizing device comprising a receiving chamber for the vessel. The exposed inlet of the gas supply channel of the first closure element is located in the receiving chamber which besides is sealed toward the ambience when the vessel has been placed in the receiving chamber. The gas entering via the inlet of the gas supply channel of the first closure element will leave the vessel again via the outlet of the first closure element. In so far, the container of the invention is practical and easily handled in that the inlet as well as the outlet of the gas supply channel can be exposed by transferring the second closure element into the opening position and can be closed by transfer into the closing position.

According to an advantageous embodiment of the invention, it is provided that, on the first closure element, a contact lens holder is arranged having a gas forwarding channel extending therethrough which is in fluid connection with the gas supply channel of the first closure element. Suitably, the contact lens holder is provided with two holding areas for contact lenses, which are designed in the form of flaps or the like. The flaps have a lattice structure and have the storage solution washing around them. The gas forwarding channel within the contact lens holder suitably extends all the way to an outlet located below said storage flaps so that the gas ascending from this outlet will flow past the contact lenses and then, at the top, will be discharged via the outlet of the first closure element.

According to an advantageous embodiment of the invention, it is further provided that the outer face of the first closure element, in the state where said element is mounted to the vessel, comprises a first outer face area extending upward from the vessel and having arranged in it said at least one inlet. In this arrangement, it is particularly suitable that the outer face of the first closure element, in the state where said element is mounted to the vessel, comprises a second outer face area arranged substantially parallel to the extension of the filling opening and having arranged in it the venting opening of the first closure element. The first closure element is suitably formed as a cap comprising a peripheral face and an end face. The peripheral face forms the above mentioned first outer face area while the end face forms the above mentioned second outer face area.

According to an advantageous embodiment, it is further provided that also the second closure element is formed in the manner of a cap which is mounted on the first closure element. In the fully mounted state, the second closure element will then cover both the gas supply channel on the peripheral wall of the first closure element and the outlet at the end wall of the first closure element.

According to a further advantageous embodiment of the invention, it is provided that the vessel comprises a bottom wall having a circumferential enclosure wall—particularly a cylindrical enclosure wall—extending upward from it, and that the filling opening of the vessel is arranged opposite to said bottom wall. Herein, it is further of advantage if the enclosure wall of the vessel comprises a circumferential edge arranged opposite to the bottom wall of the vessel and delimiting the filling opening.

It is of particular advantage if both closure elements are formed as screw closure lids and particularly as screw caps. By way of alternative, it can be provided that the first closure element can be plugged or mounted onto the vessel, or can be inserted into the filling opening, or can be fastened to the vessel by twisting, e.g. by means of a bayonet lock, and/or that the second closure element can be screwed to the first closure element while plugged or mounted thereon, or can be fastened to the first closure element by twisting, e.g. by means of a bayonet lock.

For closing the inlet as well as the outlet of the gas supply channel of the first closure element, sealing elements can be inserted on the first closure element and/or the second closure element. Particularly, it can be provided that the inlet of the gas supply channel of the first closure element is formed in the first outer face area as an annular groove at least partially surrounding the closure element, and that the first closure element comprises a sealing element on which the second closure element is in sealed abutment when covering said annular groove.

According to a further advantageous embodiment of the invention, it is provided that the second closure element comprises an outlet opening arranged at a lateral displacement relative to the venting opening of the first closure element, and that, around the venting opening of the first closure element and/or around the outlet opening of the second closure element, or on the second closure element opposite to the venting opening, and/or on the first closure element opposite to the outlet opening, there is arranged a sealing element sealingly abutted by the second and respectively the first closure element in the closed position of the second closure element.

In case that the two closure elements are each formed as a screw cap, it is of advantage if the inlet of the gas supply channel of the first screw cap is formed at the peripheral portion of the latter, and the peripheral portion of the second screw cap will cover the inlet of the gas supply channel of the first screw cap for closing the inlet, and if the venting opening of the first screw cap is formed in the end face portion of the latter and the end face portion of the second screw cap will cover the venting opening of the first screw cap for closing the venting opening, particularly by means of a sealing element.

As already mentioned above, it is quite simple under the aspect of operability if each closure element can be manually transferred from an opening position into a closing position or vice versa, wherein both closure elements will remain in the respective closing position on the vessel and respectively the first closure element, and a mechanical resistance exists against a transfer from out of the respective opening position beyond the respective closing position.

For gassing, as likewise already briefly mentioned above, the container of the invention is inserted into the receiving chamber of a unit for generating and/or releasing a cleaning and/or sterilizing gas. For this purpose, the receiving chamber comprises an insertion opening, wherein the second closure element comprises an abutment element for abutment on the insertion opening of the receiving chamber in the state where the latter receives the vessel while forming an annular space between the inlet of the gas supply channel of the first closure element and the receiving chamber, and wherein, between the insertion opening and the inlet of the gas supply channel of the first closure element, a sealing element is arranged for sealing said annular space toward the insertion opening. The sealing element can be arranged in the insertion opening of the receiving chamber or around the insertion opening of the receiving chamber for abutment on the abutment element of the second closure element or on the first closure element, between the at least one inlet opening of the gas supply channel and the abutment element of the second closure element.

The invention will be explained in greater detail hereunder by way of two embodiments and with reference to the drawing. In the several views of the drawing, the following is shown.

In FIGS. 1 to 4, there are shown various views of a container 10 for a contact lens storage solution 12 which is e.g. a physiological saline solution. Container 10, which in the present embodiment is of a tubular shape, includes a vessel 14 which in this case is cylindrical and which has a bottom wall 16 and a cylindrical enclosure wall 18 extending upward from enclosure wall 18. On its end opposite to its bottom wall 16, vessel 14 comprises a filling opening 20 (see e.g. also FIG. 7) via which the vessel 14 can be filled with the storage solution. A dual closure means 22, still to be described in greater detail further below, can be sealingly attached to the vessel 14, by way of a screw connection in the present embodiment, for closing the filling opening 20. Said dual closure means 22 comprises two closure elements 24 and 26 substantially formed as screw caps. Extending from the first closure element 24 is a contact lens holder 28 which, for accommodating two contact lenses (not shown), comprises two grid-like semi-shells or caps 30, the latter being pivotally arranged and each surrounding a contact lens and holding it in this manner.

The construction and the functionality for gassing the container 10 and for closing the container 10 can be best seen in FIGS. 2 to 6. For the purpose of gassing, container 10 will be inserted into a (placement) receiving chamber 32 of a unit 34 for generating the cleaning and/or sterilizing gas. The receiving chamber 32 comprises an insertion opening 36. The gas will be introduced into the chamber 32 via the bottom 38 of the chamber.

To allow the gas introduced into the receiving chamber 32 to enter the container 10, the latter comprises an inlet for the gas. This inlet must be exposed, which is effected by transferring the second closure element 26 from the closing position according to FIGS. 5, 6 and 7 into the opening position according to FIGS. 1, 2 and 3. In the opening position of second closure element 26, said element exposes inlets 40—in this embodiment, two inlets—of a gas supply channel 42 of the first closure element 24. Said inlets 40 are formed in the peripheral area 44 (first outer face area) of first closure element 24. The gas supply channel 42 extends substantially diametrically through the first closure element 24 and is in fluidic connection with a gas forwarding channel 46 through the contact lens holder 28 (see e.g. FIG. 2). Said gas forwarding channel 46, terminating below the semi-shells or caps 30 is fluidically connected to the gas supply channel 42 at the gas outlet 48 of the latter. The gas issuing from the gas forwarding channel 46 will rise within vessel 14 and in the process will pass along the contact lenses which are to be cleaned. The gas will escape via venting openings 50 in first closure element 24 which are arranged on both sides of gas supply channel 42 and which terminate in the end face 52 (second outer face area) of first closure element 24 (see FIGS. 3 and 4). In the open state of inlet 40, the second closure element 26 will also clear the venting openings 50, thus allowing the gas to escape. The gas will escape through the venting openings 50 and will pass through an intermediate space 54, which in the opened state of the second closure element 26 is formed between the latter and the first closure element 24, until reaching an outlet 56 of second closure element 26 (see again FIGS. 2 and 3).

Figure 2:
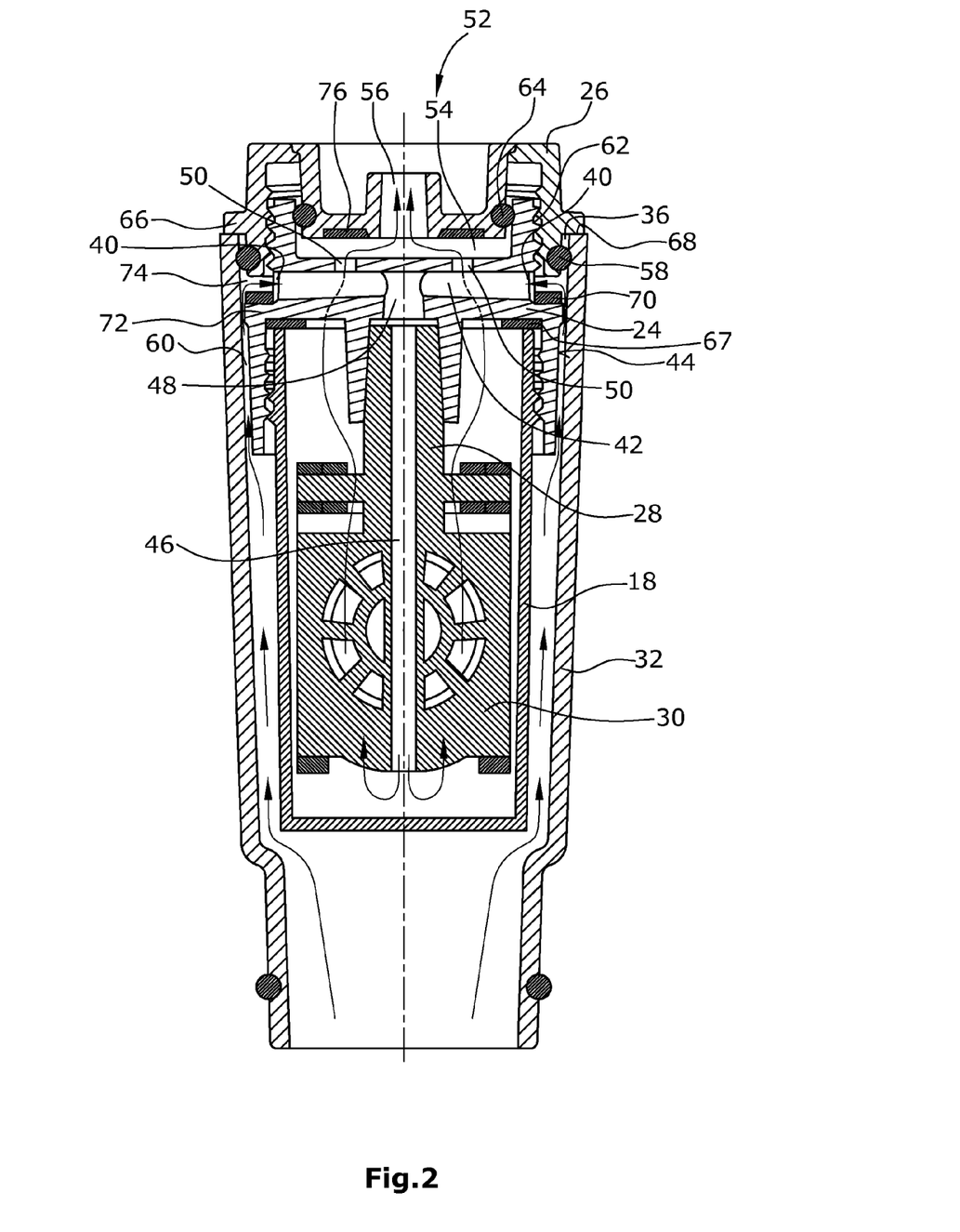
FIG. 2 is a longitudinal sectional view taken along the line II-II of the container according to FIG. 1.
Figure 3:
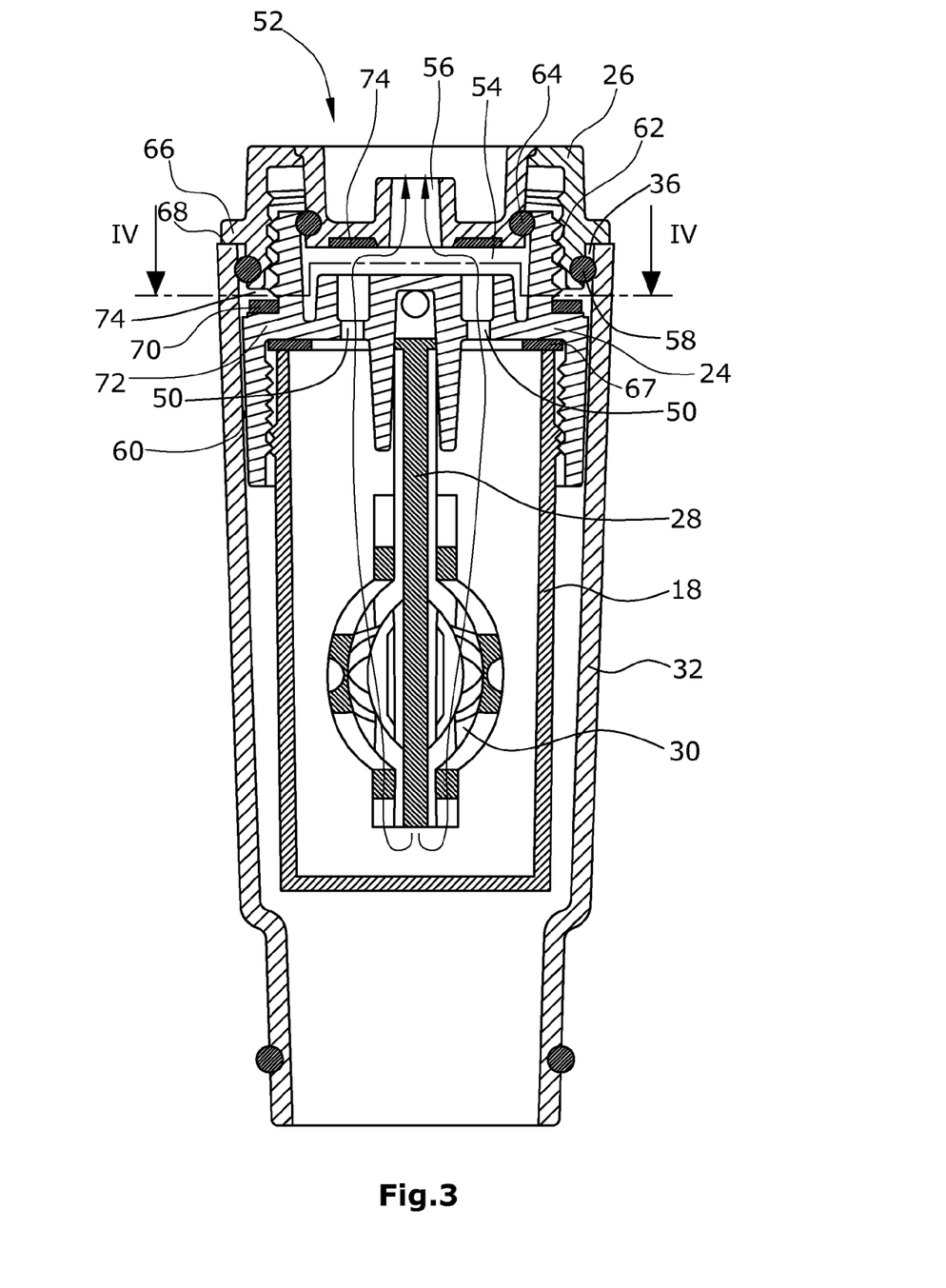
FIG. 3 is a longitudinal sectional view, oriented at 90° relative to FIG. 2, of the container according to FIG. 1.
Figure 4:
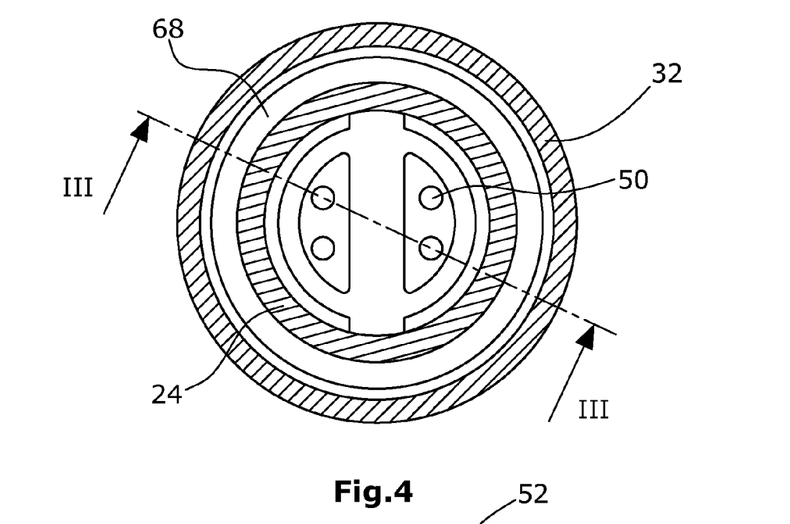
FIG. 4 is a sectional view taken along the line IV-IV of FIG. 3.
Figure 5:
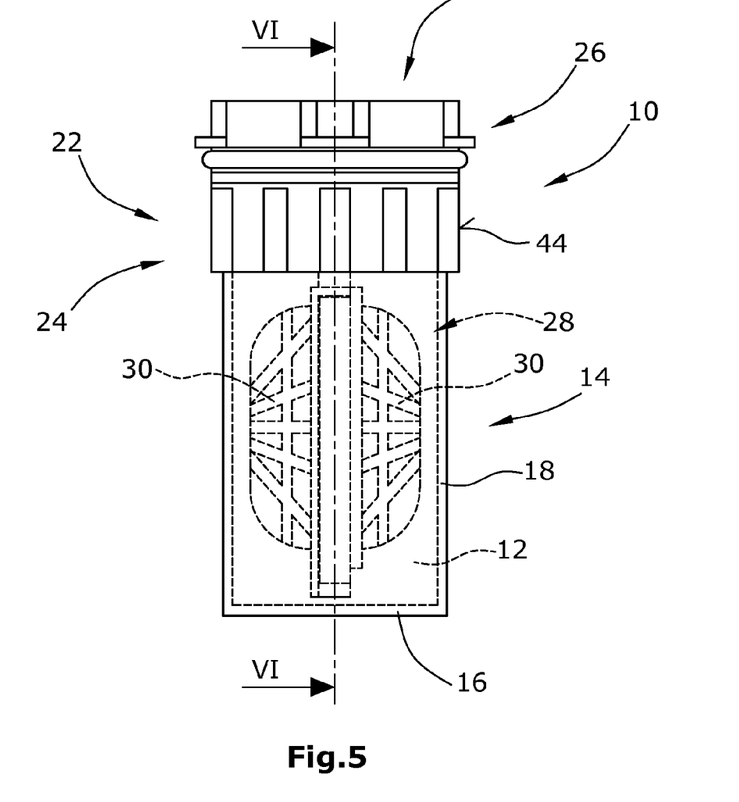
FIG. 5 is a lateral view of the container with the second closure element arranged in its closing position.

As is best evident from FIG. 2, the second closure element 26 comprises a sealing ring 58 which is arranged within the insertion opening 36 of the receiving chamber 32 when the container 10 has been inserted into receiving chamber 32. By means of this sealing ring 58, the annular space 60 forming between the first closure element 24 and the receiving chamber 32 is sealed toward the insertion opening 36 and thus toward the ambience. Gas which possibly might be flowing through the threaded engagement 62 between the two closure elements 24,26, will be prevented from leaking into the ambience by means of a further sealing ring 64 between second closure element 26 and first closure element 24. Second closure element 26 comprises an abutment element 66, in the present embodiment formed as a radially outward flange, by which it is supported on the edge 68 of receiving chamber 32.

Thus, in the above described position of use of container 10 for gassing the vessel 14 of the container, the first closure element 24 is sealingly connected to vessel 14 and closes the filling opening 20 of the vessel (see also sealing 67), while the second closure element 26 is in its opening position in which both the gas supply channel openings 40 and the venting openings 50 are exposed and thus opened. If required, gas issuing from the venting openings 50 of first closure element 24 or from the opening 56 of second closure element 26 can be neutralized by a (non-illustrated) neutralization material (e.g. formed as filter) along or through which the gas will flow. This neutralization material can be arranged outside on the closure element 26 and be fixed by a holding element (e.g. a cap or the like mounted to the closure element 26), wherein a venting effect is to be provided through the holding element or between the holding element and the second closure element 26 (and, if the holding element also engages the first closure element 24, also between the holding element and the first closure element), which, however, can also be realized by means of a filter comprising the neutralization material.

After the gassing process, the container 10 will be removed from the receiving chamber 32, and the second closure element 26 is transferred into its closing position by threaded engagement with the first closure element 24, wherein, in the closing position, both the inlets 40 and the venting openings 50 are closed. This condition is enhanced by a flat annular sealing 70 provided on a surrounding shoulder 72 on the first closure element 24. Said shoulder forms a flank of a surrounding annular groove 74.

Figure 6:
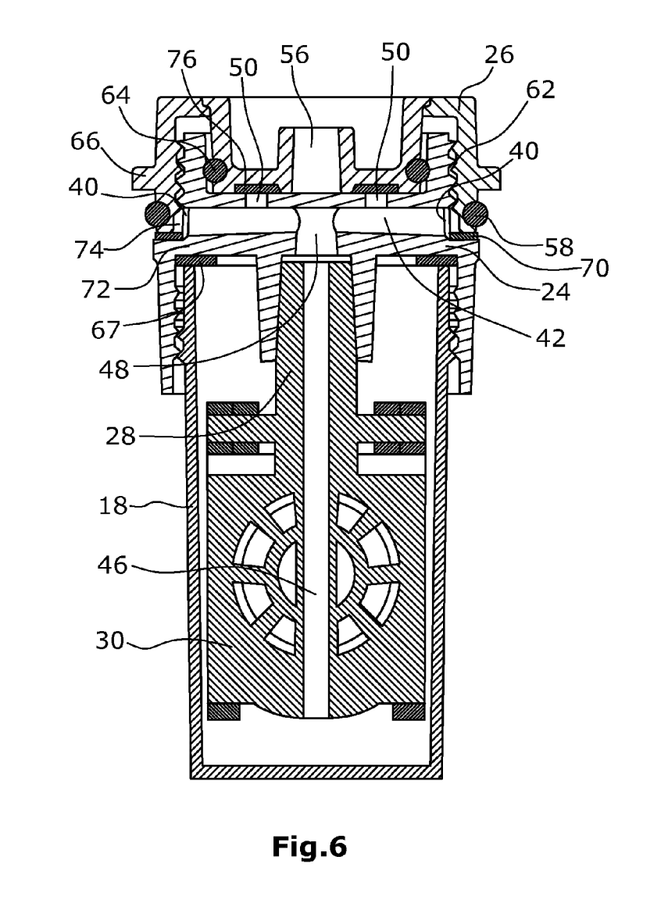
FIG. 6 is a longitudinal sectional view, taken along the line VI-VI of FIG. 5, of the container in its closed state.
Figure 7:
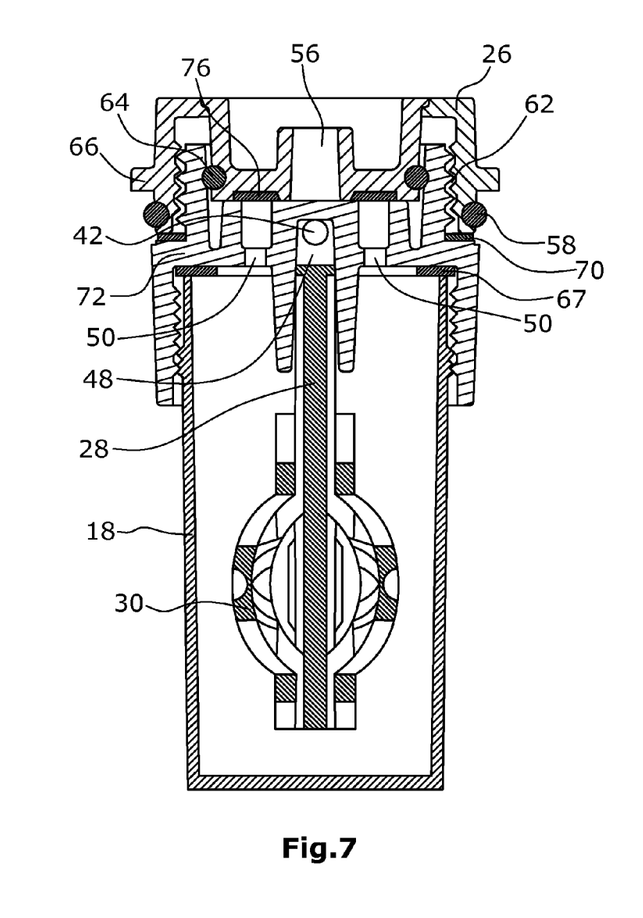
FIG. 7 is a longitudinal sectional view, oriented at 90° relative to FIG. 6, of the container in its closed state.

The venting openings 50 are closed by a sealing disk 76 which is arranged on the second closure element 26, namely opposite to the venting openings 50. This situation is depicted in FIGS. 6 and 7.

Figure 8:
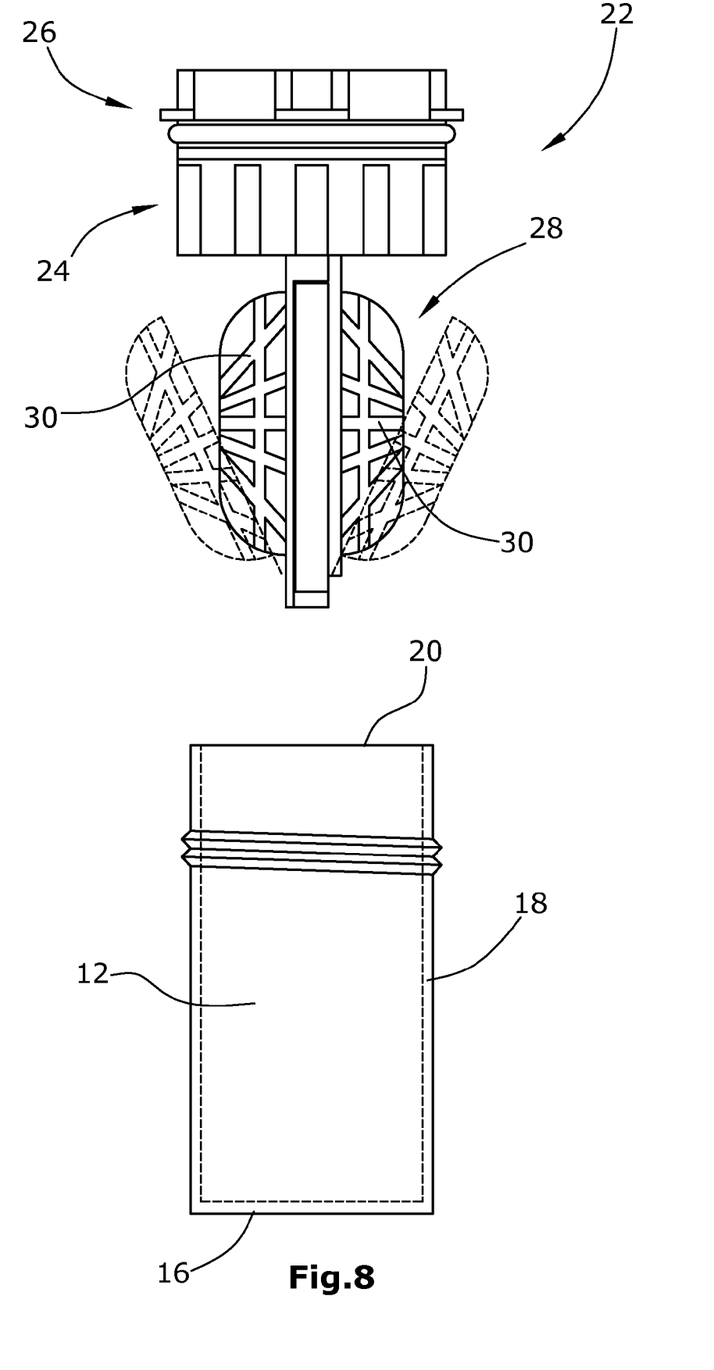
FIG. 8 is a view of the container as shown in the previous Figures, wherein the dual closure means has been removed and the container thus is open.

To make it possible now to remove the contact lenses or, first, the contact lens holder 28, from the vessel 14, the first closure element 24 will be unscrewed from the vessel 14 while, in the process, the relative position between the first and the second closure element 24 and resp. 26 is maintained, i.e. the second closure element 26 remains in its closing position. This situation is illustrated e.g. in FIG. 8.

Figure 1:
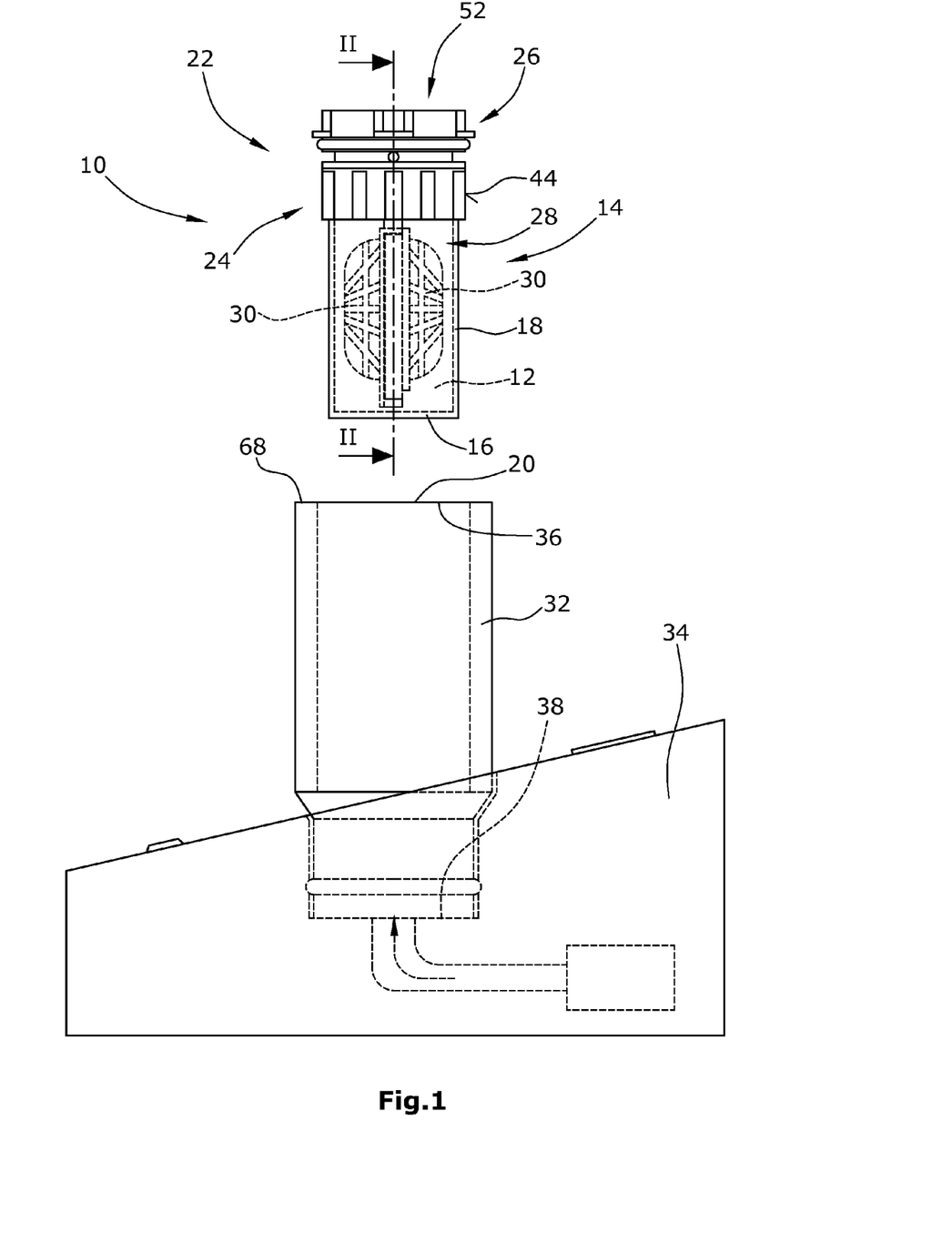
FIG. 1 is a lateral view of a unit for generating a cleaning and/or sterilizing gas such as e.g. hydrogen peroxide or ozone, with a mounted receiving chamber for a container according to an embodiment of the invention.
Figure 9:
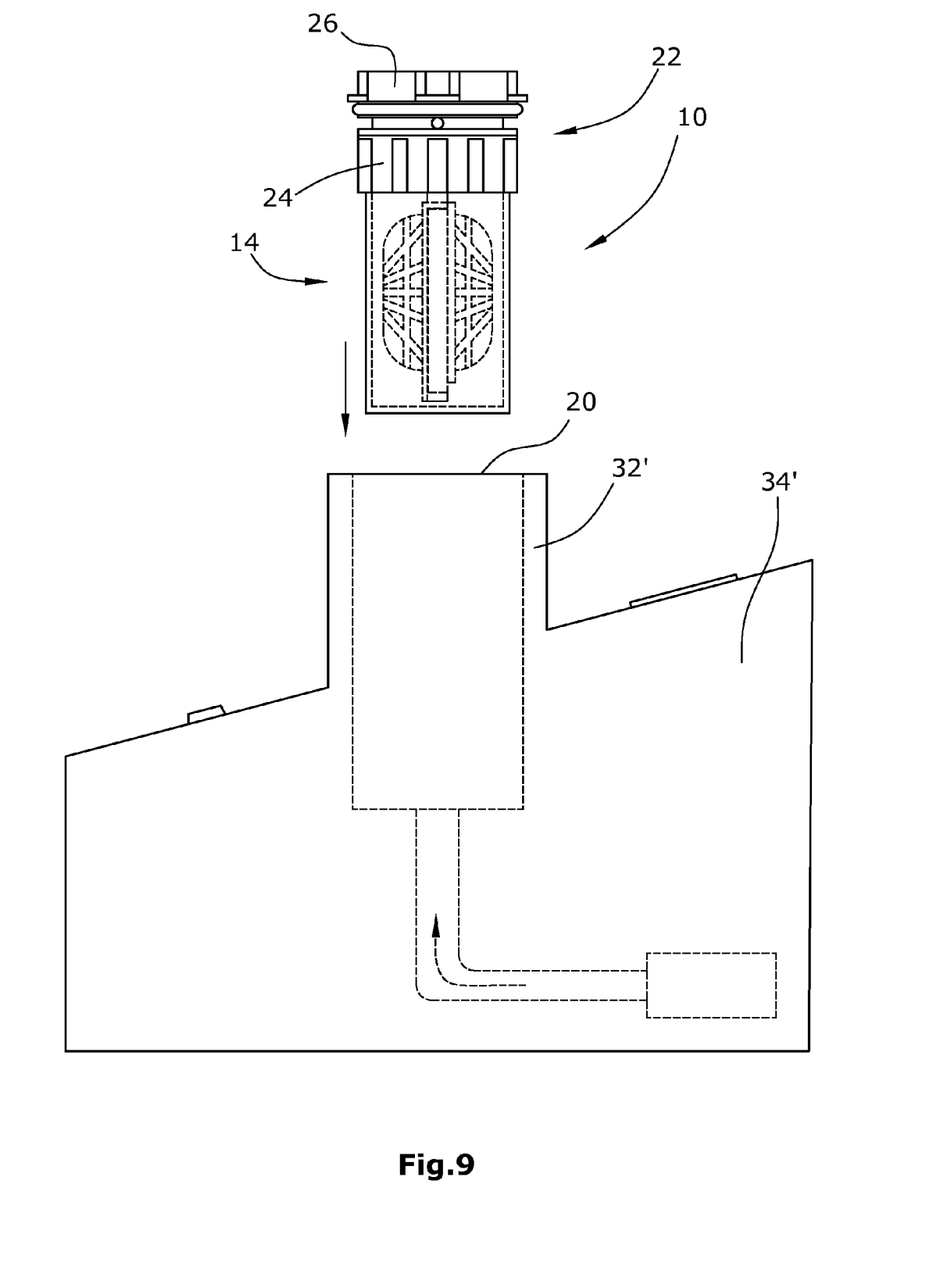
FIG. 9 is a view of an alternatively designed unit for generating a cleaning and/or sterilizing gas, comprising a container receiving chamber formed integrally with said unit.

FIG. 9 shows an embodiment of a unit 34 for generating the cleaning and/or sterilizing gas, wherein the receiving chamber 32 is not designed to be inserted into the receiving portion of a housing of unit 34 according to FIG. 1, but is inserted into the receiving chamber 32' formed integrally with the housing of unit 34'. The container 10 which is insertable into the receiving chamber 32', is designed in the manner described with reference to the previous Figures.

As mentioned farther above, the cleaning and/or sterilizing gasses (e.g. ozone) which are discharged from the venting openings 50 during the gassing of the interior of the vessel 14 can be neutralized by a (neutralization) filter (e.g. active carbon filter). However, due to the gassing—which preferably will be terminated automatically—performed by the unit 34 for generating theses gases, a fluid connection will exist between the ambience and the interior of the vessel 14 via the venting openings 50 (and the filter). In this phase, there could thus occur a decontamination of the interior of the vessel and, consequently, of the contact lens and the storage solution. In order to prevent this, it appears advisable to provide a one-way or back-check valve in the area of the venting openings 50 (i.e. upstream or downstream thereof) or upstream or downstream of the optional (neutralization) filters, wherein this valve will automatically open under the effect of the pressure of the discharged gases and will then automatically close when this pressure has ceased. Such a valve can comprise a valve body which under a biasing force or under the influence of its own weight is in sealing abutment on a valve seat of the valve. In case of an applied gas flow, the valve body will be automatically lifted or, put in more-general terms, be moved away from the valve seat. Generally, the valve body can be of any desired design and can be formed e.g. as a movable piston or cone, or as a movable ball. Alternatively, the valve can also comprise a disk- or flap-shaped, optionally flexible valve body which will cover the venting openings 50 in the closed position and, for instance, because of its flexible attachment, will at least in a partial area move away from the venting openings and clear the venting openings for venting the vessel during gassing.

As a matter of course, the valve and all other component parts of the vessel which are in contact with the cleaning and/or sterilizing gas and the storage solution, are inert toward the gas and the solution.

The invention claimed is:

1. A container for a contact lens storage solution, in particular having contact lenses in said contact lens storage solution, said container comprising
    a vessel having a filling opening,
    a first closing element attachable to the vessel for closing the filling opening,
    the first closing element comprising a gas supply channel for a cleaning and/or sterilizing gas, which extends from at least one inlet on an outer face of the first closing element to at least one outlet on an inner face of the first closing element facing the interior of the vessel, and
    said first closing element comprising, on its outer face, at least one venting opening for the escape of gas from the vessel, and
    a second closing element arranged on the first closing element, for closing the at least one inlet of the gas supply channel and the at least one venting opening of the first closing element; and
    wherein the second closure element comprises an outlet opening arranged at a lateral displacement relative to the venting opening of the first closure element, and that, around the venting opening of the first closure element, and/or around the outlet opening of the second closure element, or on the second closure element opposite to the venting opening, and/or on the first closure element opposite to the outlet opening, a sealing element is arranged which is sealingly abutted by the second and respectively the first closure element in the closed position of the second closure element.

2. The container according to claim 1, wherein the first closing element has arranged on it a contact lens holder with a gas forwarding channel extending therethrough which is in fluid connection with the gas supply channel of the first closing element.

3. The container according to claim 1, wherein the outer face of the first closing element, in the state where said element is mounted to the vessel, comprises a first outer face area extending upward from the vessel and having arranged in it the at least one inlet.

4. The container according to claim 3, wherein the second closure element in a closing position covers both said at least one gas supply channel inlet and the venting opening of the first closure element.

5. The container according to claim 3, wherein the inlet of the gas supply channel of the first closure element is formed in the first outer face area as an annular groove at least partially surrounding the closure element, and the second closure element is in sealed abutment with the sealing element when covering said annular groove.

6. The container according to claim 1, wherein the outer face of the first closure element, in the state where said element is mounted to the vessel, comprises a second outer face area arranged substantially parallel to the extension of the filling opening and having arranged in it the venting opening of the first closure element.

7. The container according to claim 1, wherein the vessel comprises a bottom wall having a circumferential enclosure wall extending upward from it, and that the filling opening of the vessel is arranged opposite to said bottom wall.

8. The container according to claim 7, wherein the enclosure wall of the vessel comprises a circumferential edge arranged opposite to the bottom wall of the vessel and delimiting the filling opening.

9. The container according to claim 1, wherein the first closure element can be plugged or mounted onto the vessel, or can be inserted into the filling opening, or can be fastened to the vessel by threaded engagement or can be fastened to the vessel by twisting, and/or that the second closure element can be plugged or mounted to the first closure element, or can be fastened to the first closure element by threaded engagement or can be fastened to the first closure element by twisting.

10. The container according to claim 1, wherein both closure elements are formed as first and respectively second screw closure lids, the first screw closure lid being adapted for threaded engagement with the vessel and the second screw closure lid being adapted for threaded engagement with the first screw closure lid.

11. The container according to claim 10, wherein said screw closure lids are formed as first and respectively second screw caps which each comprise a peripheral portion and an end side portion on their outer faces.

12. The container according to claim 11, wherein the inlet of the gas supply channel of the first screw cap is formed at the peripheral portion of the first screw cap, and the peripheral portion of the second screw cap covers the inlet of the gas supply channel of the first screw cap for closing the inlet, and that the venting opening of the first screw cap is formed in the end face portion of the first screw cap and the end face portion of the second screw cap covers the venting opening of the first screw cap for closing the venting opening.

13. A cleaning and/or sterilizing device for contact lenses arranged in a contact lens storage solution, said device comprising
    a container according to claim 1, and
    a unit provided for generating and/or releasing a cleaning and/or sterilizing gas, said unit comprising a receiving chamber including an insertion opening and provided for receiving the vessel, wherein the second closure element comprises an abutment element for abutment on the insertion opening of the receiving chamber in the state where the receiving chamber receives the vessel while forming an annular space between the inlet of the gas supply channel of the first closure element and the receiving chamber, and that, between the insertion opening and the inlet of the gas supply channel of the first closure element, a further sealing element is arranged for sealing said annular space toward the insertion opening.

14. The cleaning and/or sterilizing device according to claim 13, wherein said receiving chamber is formed integrally with said unit provided for generating and/or releasing a cleaning and/or sterilizing gas, or is a component which is separated from said unit and insertable into a receiving portion in said unit.

15. A container for a contact lens storage solution, in particular having contact lenses in said contact lens storage solution, said container comprising
    a vessel having a filling opening,
    a first closing element attachable to the vessel for closing the filling opening,
    the first closing element comprising a gas supply channel for a cleaning and/or sterilizing gas, which extends from at least one inlet on an outer face of the first closing element to at least one outlet on an inner face of the first closing element facing the interior of the vessel, and said first closing element comprising, on its outer face, at least one venting opening for the escape of gas from the vessel, and a second closing element arranged on the first closing element, for closing the at least one inlet of the gas supply channel and the at least one venting opening of the first closing element, and wherein each closure element can be manually transferred from an opening position into a closing position or vice versa, wherein both closure elements remain in the respective closing position on the vessel and respectively the first closure element, and a mechanical resistance exists against a transfer from out of the respective closing position beyond the respective opening position and vice versa.

16. The container according to claim 15, wherein by a receiving chamber comprising an insertion opening and provided for receiving the vessel, wherein the second closure element comprises an abutment element for abutment on the insertion opening of the receiving chamber in the state where the receiving chamber receives the vessel while forming an annular space between the inlet of the gas supply channel of the first closure element and the receiving chamber, and that, between the insertion opening and the inlet of the gas supply channel of the first closure element, a sealing element is arranged for sealing said annular space toward the insertion opening.

17. The container according to claim 16, wherein the sealing element is arranged in the insertion opening of the receiving chamber or around the insertion opening of the receiving chamber so as to be in abutment on said abutment element of the second closure element or on the first closure element, the latter abutment between the at least one inlet of the gas supply channel and the abutment element of the second closure element.

18. A container for a contact lens storage solution, in particular having contact lenses in said contact lens storage solution, said container comprising a vessel having a filling opening, a first closing element attachable to the vessel for closing the filling opening, the first closing element comprising a gas supply channel for a cleaning and/or sterilizing gas which extends from at least one inlet on an outer face of the first closing element to at least one outlet on an inner face of the first closing element facing the interior of the vessel, and said first closing element comprising, on its outer face, at least one venting opening for the escape of gas from the vessel, and a second closing element arranged on the first closing element, for closing the at least one inlet of the gas supply channel and the at least one venting opening of the first closing element, and wherein the second closure element comprises a neutralization material for neutralizing gas escaping from the venting opening of the first closure element prior to escape of said gas into the ambience.

* * * * *